(12) United States Patent
Conn

(10) Patent No.: US 7,695,917 B2
(45) Date of Patent: Apr. 13, 2010

(54) RESCUE OF GONADOTROPIN RELEASING HORMONE RECEPTOR MUTANTS

(75) Inventor: P. Michael Conn, Portland, OR (US)

(73) Assignee: Oregon Health & Science University, Portland, OR (US)

(*) Notice: Subject to any disclaimer, the term of this patent is extended or adjusted under 35 U.S.C. 154(b) by 1416 days.

(21) Appl. No.: 10/492,295

(22) PCT Filed: Oct. 8, 2002

(86) PCT No.: PCT/US02/32399

§ 371 (c)(1),
(2), (4) Date: Apr. 8, 2004

(87) PCT Pub. No.: WO03/038036

PCT Pub. Date: May 8, 2003

(65) Prior Publication Data

US 2004/0191251 A1 Sep. 30, 2004

Related U.S. Application Data

(60) Provisional application No. 60/328,319, filed on Oct. 9, 2001, provisional application No. 60/376,685, filed on Apr. 29, 2002.

(51) Int. Cl.
*G01N 33/53* (2006.01)
*C07D 451/00* (2006.01)
(52) U.S. Cl. .................. 435/7.1; 530/313; 546/124
(58) Field of Classification Search .................. None
See application file for complete search history.

(56) References Cited

U.S. PATENT DOCUMENTS 6,200,957 B1    3/2001   Goulet et al.
6,270,954 B1    8/2001   Welch et al.

FOREIGN PATENT DOCUMENTS

WO    WO 97/37645 A1    10/1997

OTHER PUBLICATIONS

Brothers et al., "Unexpected Effects of Epitope and Chimeric Tags on Gonadotropin-Releasing Hormone Receptors: Implications for Understanding the Molecular Etiology of Hypogonadotropic Hypogonadism," *J. Clin. Endocrinol. Metab.* 88:6107-6112 (2003).
Janovick et al., "Evolved Regulation of Gonadotropin-Releasing Hormone Receptor Cell Surface Expression," *Endocrine* 22:317-327 (2003).
Kaykas et al., "Mutant Frizzled 4 Associated with Vitreoretinopathy Traps Wild-Type Frizzled in the Endoplasmic Reticulum by Oligomerization," *Nat. Cell Biol.* 6:52-58 (2004).
Leaños-Miranda et al., "Dominant-Negative Action of Disease-Causing Gonadotropin-Releasing Hormone Receptor (GnRHR) Mutants: A Trait that Potentially Coevolved with Decreased Plasma Membrane Expression of GnRHR in Humans," *J. Clin. Endocrinol. Metab.* 88:3360-3367 (2003).
Ulloa-Aguirre et al., "Misrouted Cell Surface Receptors as a Novel Disease Aetiology and Potential Therapeutic Target: The Case of Hypogonadotropic Hypogonadism Due to Gonadotropin-Releasing Hormone Resistance," *Expert Opin. Ther. Targets* 7:175-185 (2003).
Ulloa-Aguirre et al., "Misrouted Cell Surface GnRH Receptors as a Disease Aetiology for Congenital Isolated Hypogonadotrophic Hypoganadism," *Human Reprod. Update* 10:1-16 (2004).
Burlingham et al., "An Intuitive Look at the Relationship of $K_i$ and $IC_{50}$: A More General Use for the Dixon Plot," *J. Chem. Ed.* 80:214-218 (2003).
Conn et al., "Protein Origami—Therapeutic Rescue of Misfolded Gene Products," *Mol. Interv.* 2:308-316 (2002).
Edwards et al., Localization of G-protein-Coupled Receptors in Health and Disease, *Trends Pharmacol. Sci.* 21:304-308 (2000).
Huckle and Conn, "Use of Lithium Ion in Measurement of Stimulated Pituitary Inositol Phospholipid Turnover," *Meth. Enzymol.* 141:149-155 (1987).
Huckle et al., "Differential Sensitivity of Agonist- and Antagonist-Occupied Gonadotropin-Releasing Hormone Receptors to Protein Kinase C Activators," *J. Biol. Chem.* 263:3296-3302 (1988).
Janovick et al., "Rescue of Hypogonadotropic Hypogonadism-Causing and Manufactured GnRH Receptor Mutants by a Specific Protein-Folding Template: Misrouted Proteins as a Novel Disease Etiology and Therapeutic Target," *J. Clin. Endocrinol. Metab.* 87:3255-3262 (2002).
Janovick et al., "Structure-Activity Relations of Successful Pharmacologic Chaperones for Rescue of Naturally Occurring and Manufactured Mutants of the Gonadotropin-Releasing Hormone Receptor," *J. Pharmacol. Exper. Ther.* 305:608-614 (2003).
Leaños-Miranda et al., "Receptor-Misrouting: An Unexpectedly Prevalent and Rescuable Etiology in Gonadotropin-Releasing Hormone Receptor-Mediated Hypogonadotropic Hypogonadism," *J. Clin. Endocrinol. Metab.* 87:4825-4828 (2002).
Morello et al., "Pharmacological Chaperones Rescue Cell-Surface Expression and Function of Misfolded V2 Vasopressin Receptor Mutants," *J. Clin. Invest.* 105:887-895 (2000).
Morello et al., "Pharmacological Chaperones: A New Twist on Receptor Folding," *Trends Pharmacol. Sci.* 21:466-469 (2000).

*Primary Examiner*—Dong Jiang
(74) *Attorney, Agent, or Firm*—Klarquist Sparkman, LLP

(57) ABSTRACT

Herein disclosed is a method of rescuing gonadotropin-releasing hormone receptor (GnRHR) mutants with IN3 or a mimetic thereof. IN3 significantly rescues 11 missense mutations as assessed by radioligand binding and by IP production. Such rescue occurred despite widely disparate loci along the receptor. In addition, many altered GnRH receptors (terminally truncated, internal deletions, or lacking the ability to form bridges to form tertiary structure) were rescued with IN3.

6 Claims, 5 Drawing Sheets

```
                        SEQUENCE LISTING

<160> NUMBER OF SEQ ID NOS: 1

<210> SEQ ID NO 1
<211> LENGTH: 328
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa can be Asn or Lys
<220> FEATURE:
<221> NAME/KEY: MISC_FEATURE
<222> LOCATION: (32)..(32)
<223> OTHER INFORMATION: Xaa can be Thr or Ile
<220> FEATURE:
<221> NAME/KEY: MISC_FEATURE
<222> LOCATION: (90)..(90)
<223> OTHER INFORMATION: Xaa can be Glu or Lys
<220> FEATURE:
<221> NAME/KEY: MISC_FEATURE
<222> LOCATION: (106)..(106)
<223> OTHER INFORMATION: Xaa can be Gln or Arg
<220> FEATURE:
<221> NAME/KEY: MISC_FEATURE
<222> LOCATION: (129)..(129)
<223> OTHER INFORMATION: Xaa can be Ala or Asp
<220> FEATURE:
<221> NAME/KEY: MISC_FEATURE
<222> LOCATION: (139)..(139)
<223> OTHER INFORMATION: Xaa can be Arg or His
<220> FEATURE:
<221> NAME/KEY: MISC_FEATURE
<222> LOCATION: (168)..(168)
<223> OTHER INFORMATION: Xaa can be Ser or Arg
<220> FEATURE:
<221> NAME/KEY: MISC_FEATURE
<222> LOCATION: (200)..(200)
<223> OTHER INFORMATION: Xaa can be Cys or Tyr
<220> FEATURE:
<221> NAME/KEY: MISC_FEATURE
<222> LOCATION: (217)..(217)
<223> OTHER INFORMATION: Xaa can be Ser or Arg
<220> FEATURE:
<221> NAME/KEY: MISC_FEATURE
<222> LOCATION: (262)..(262)
<223> OTHER INFORMATION: Xaa can be Gln or Arg
<220> FEATURE:
<221> NAME/KEY: MISC_FEATURE
<222> LOCATION: (266)..(266)
<223> OTHER INFORMATION: Xaa can be Leu or Arg
<220> FEATURE:
<221> NAME/KEY: MISC_FEATURE
<222> LOCATION: (279)..(279)
<223> OTHER INFORMATION: Xaa can be Cys or Tyr
<220> FEATURE:
<221> NAME/KEY: MISC_FEATURE
<222> LOCATION: (284)..(284)
<223> OTHER INFORMATION: Xaa can be Cys or Tyr
<220> FEATURE:
<221> NAME/KEY: MISC_FEATURE
<222> LOCATION: (314)..(314)
<223> OTHER INFORMATION: Xaa can be Leu or no amino acid

<400> SEQUENCE: 1

Met Ala Asn Ser Ala Ser Pro Glu Gln Xaa Gln Asn His Cys Ser Ala
1               5                   10                  15
```

```
Ile Asn Asn Ser Ile Pro Leu Met Gln Gly Asn Leu Pro Thr Leu Xaa
            20              25              30

Leu Ser Gly Lys Ile Arg Val Thr Val Thr Phe Phe Leu Phe Leu Leu
            35              40              45

Ser Ala Thr Phe Asn Ala Ser Phe Leu Leu Lys Leu Gln Lys Trp Thr
    50              55              60

Gln Lys Lys Glu Lys Gly Lys Lys Leu Ser Arg Met Lys Leu Leu Leu
65              70              75              80

Lys His Leu Thr Leu Ala Asn Leu Leu Xaa Thr Leu Ile Val Met Pro
            85              90              95

Leu Asp Gly Met Trp Asn Ile Thr Val Xaa Trp Tyr Ala Gly Glu Leu
            100             105             110

Leu Cys Lys Val Leu Ser Tyr Leu Lys Leu Phe Ser Met Tyr Ala Pro
            115             120             125

Xaa Phe Met Met Val Val Ile Ser Leu Asp Xaa Ser Leu Ala Ile Thr
130             135             140

Arg Pro Leu Ala Leu Lys Ser Asn Ser Lys Val Gly Gln Ser Met Val
145             150             155             160

Gly Leu Ala Trp Ile Leu Ser Xaa Val Phe Ala Gly Pro Gln Leu Tyr
                165             170             175

Ile Phe Arg Met Ile His Leu Ala Asp Ser Ser Gly Gln Thr Lys Val
            180             185             190

Phe Ser Gln Cys Val Thr His Xaa Ser Phe Ser Gln Trp Trp His Gln
    195             200             205

Ala Phe Tyr Asn Phe Phe Thr Phe Xaa Cys Leu Phe Ile Ile Pro Leu
    210             215             220

Phe Ile Met Leu Ile Cys Asn Ala Lys Ile Ile Phe Thr Leu Thr Arg
225             230             235             240

Val Leu His Gln Asp Pro His Glu Leu Gln Leu Asn Gln Ser Lys Asn
            245             250             255

Asn Ile Ile Arg Ala Xaa Leu Lys Thr Xaa Lys Met Thr Val Ala Phe
            260             265             270

Ala Thr Ser Phe Thr Val Xaa Trp Thr Pro Tyr Xaa Val Leu Gly Ile
    275             280             285

Trp Tyr Trp Phe Asp Pro Glu Met Leu Asn Arg Leu Ser Asp Pro Val
    290             295             300

Asn His Phe Phe Phe Leu Phe Ala Phe Xaa Asn Pro Cys Phe Asp Pro
305             310             315             320

Leu Ile Tyr Gly Tyr Phe Ser Leu
            325
```

RESCUE OF GONADOTROPIN RELEASING HORMONE RECEPTOR MUTANTS

CROSS REFERENCE TO RELATED APPLICATIONS

This is the U.S. National Stage of International Application No. PCT/US02/32399 filed Oct. 8, 2002 (published in English under PCT Article 21(2)), which in turn claims the benefit of U.S. Provisional application No. 60/328,319 filed Oct. 9, 2001 and U.S. Provisional application No. 60/376,685 filed Apr. 29, 2002.

ACKNOWLEDGEMENT OF GOVERNMENT SUPPORT

Some of the work described in this patent application was funded by grants HD-19899, RR-00163, HD-18185 and TW/HD-00668 from the National Institutes of Health. The government may have certain rights in this invention.

FIELD

This disclosure relates to methods of rescuing gonadotropin-releasing hormone receptor (GnRHR) mutants.

BACKGROUND

Gonadotropin-releasing hormone (GnRH) plays a central role in neural regulation of reproductive function. This decapeptide is produced by specialized neurons found in the mediobasal hypothalamus, the axons of which project to the median eminence. From there, GnRH enters the portal circulation and binds to a specific receptor on pituitary gonadotropes, stimulating the synthesis and release of the gonadotropins LH and FSH. Sequence analysis of the GnRH receptor (GnRHR) is consistent with the seven transmembrane domain motif, characteristic of the G protein-coupled receptors superfamily (Ulloa-Aguirre and Conn. G protein-coupled receptors and the G protein family. In: Handbook of Physiology-Endocrinology. Section 7 Cellular Endocrinology Conn PM, ed. New York: Oxford University Press, 87-124, 1998). Human GnRHR (hGnRHR) is coupled to the $G_{q/11}$ system; after GnRH binding, the activated GnRHR-$G_{q/11}$ protein complex activates the membrane-associated enzyme phospholipase Cp, leading to inositol 1,4,5-trisphosphate (IP) production and the release of intracellular calcium (Kaiser et al., *Endocr. Rev.* 18:46-70, 1997).

Some forms of congenital hypogonadotropic hypogonadism (HH) result from mutational defects in the synthesis or action of GnRH itself. HH presents as a wide clinical spectrum, characterized by delayed sexual development and by inappropriately low or apulsatile gonadotropin and sex steroid levels, in the absence of anatomical or functional abnormalities of the hypothalamic-pituitary axis. This disorder is genetically heterogeneous and may be sporadic or familial (X-linked or autosomal).

To date, 14 mutations of the GnRHR have been described which are associated with HH. One is a truncation mutant, eight are compound heterozygotes (de Roux et al., *N. Engl. J. Med.* 337:1597-1602, 1997; Layman et al., *Nature Genetics* 18:14-15, 1998; Caron et al., *J. Clin. Endocrinol. Metab.* 84:990-6, 1999; de Roux et al., *J. Clin. Endocrinol. Metab.* 84:567-72, 1999; Kottler et al., *J. Clin. Endocrinol. Metab.* 85:3002-8, 2000; Beranova et al., *J. Clin. Endocrinol. Metab.* 86:1580-8, 2001; Pralong et al., *J. Clin. Endocrinol. Metab.* 84: 3811-6, 1999; Costa et al., *J. Clin. Endocrinol. Metab.* 86:2680-6, 2001), and five are compound homozygotes (Pralong et al., *J. Clin. Endocrinol. Metab.* 84: 3811-6, 1999; Soderlund et al., *Clin. Endocrinol.* (Oxf) 54:493-8, 2001; Pitteloud. et al., *J. Clin. Endocrinol. Metab.* 86:2470-5, 2001). These mutations are widely distributed across the entire sequence of the GnRHR (see FIG. 1). Expression in heterologous cell systems that express each naturally-occurring GnRHR mutant separately show that some mutants are totally non-functional ($E^{90}K$, $A^{129}D$, $R^{139}H$, $S^{168}R$, $C^{200}Y$, $S^{217}R$, $L^{266}R$, $C^{279}Y$, and $L^{314}X$) while others retain a modest degree of function ($N^{10}K$, $T^{32}I$, $Q^{106}R$, $R^{262}Q$, and $Y^{284}C$). It was believed that these mutations interfere with ligand binding or preclude interaction with effector proteins.

Mutant $E^{90}K$ has been 'rescued' by deleting $K^{191}$ (which, when present, decreases expression of hGnRHR at the plasma membrane) or by adding a C-terminal sequence (Maya-Nudez et al., *J. Clinical Endocrinol. Metab.* 87:2144-9, 2002). In addition, previous approaches to correct defective receptors include genetic approaches, such as increased receptor expression to produce larger numbers of receptors (Cheng et al., *Am. J. Physiol.* 268:L615-24, 1995), and the use of non-specific protein stabilizing agents to stabilize extant molecules rendered incompetent by genetic defects, such as polyols and sugars (Back et al. *Biochemistry* 18:5291-6, 1979; Brown et al., *J. Clin. Invest.* 99:1432-44, 1997; Brown et al., *Cell Stress Chaperones* 1:117-24, 1996). However, rescue by these genetic approaches is not therapeutically significant because such a method is not presently practical for in vivo use. Therefore, there is a need for a method to rescue mutant GnRHR molecules which can be used therapeutically in vivo.

SUMMARY OF THE DISCLOSURE

Herein disclosed is a method of pharmacological rescue, as assessed by ligand binding and restoration of receptor coupling to effector, of 11 naturally occurring gonadotropin releasing hormone receptor mutants (N10K, T32I, E90K, Q106R, A129D, R139H, C200Y, R262Q, L266R, C279Y, and Y284C; see FIG. 1), identified from patients with HH, as well as rescue of other defective receptors with internal or terminal deletions or substitutions at sites thought to be involved in establishment of tertiary receptor structure. The pharmacological agent used, IN3, is a small membrane permeant molecule, originally designed as an orally-active, non-peptide receptor antagonist. However, IN3 appears to function as a folding template, capable of correcting the structural defects caused by the GnRHR mutations thereby restoring function. After rescue, IN3 can be removed. The rescued mutant GnRHR, now stabilized in the plasma membrane, couples ligand binding to activation of the appropriate effector system.

The data presented herein indicate that mutant GnRHRs have frequently not lost intrinsic functionality and are subject to rescue by agents such as IN3 that enhance membrane expression. For example, defective protein folding of mutant GnRHRs may result in failure of the receptor to reach the protein's proper locus within the cell, but may retain the ability to bind hormone and couple to effectors.

The disclosed method does not require genetic manipulation and offers high specificity, since IN3 is a specific hGnRHR antagonist (Ashton et al., Bioorg. Med. Chem. Lett. 11:2597-602, 2001; Ashton et al., *Bioorg. Med. Chem. Lett.* 11:1727-31, 2001; Ashton et al., *Bioorg. Med. Chem. Lett.* 11:1723-6, 2001). The methods disclosed herein can be used to assess ligand binding and effector coupling of mutants previously not expressed at measurable levels, or to increase levels of the WT receptor without exposure to (up-regulating) hormone.

The foregoing and other objects, features, and advantages of the disclosure will become more apparent from the following detailed description of several embodiments which proceeds with reference to the accompanying figures.

DETAILED DESCRIPTION OF SEVERAL EMBODIMENTS

Abbreviations and Terms

Figure 1:
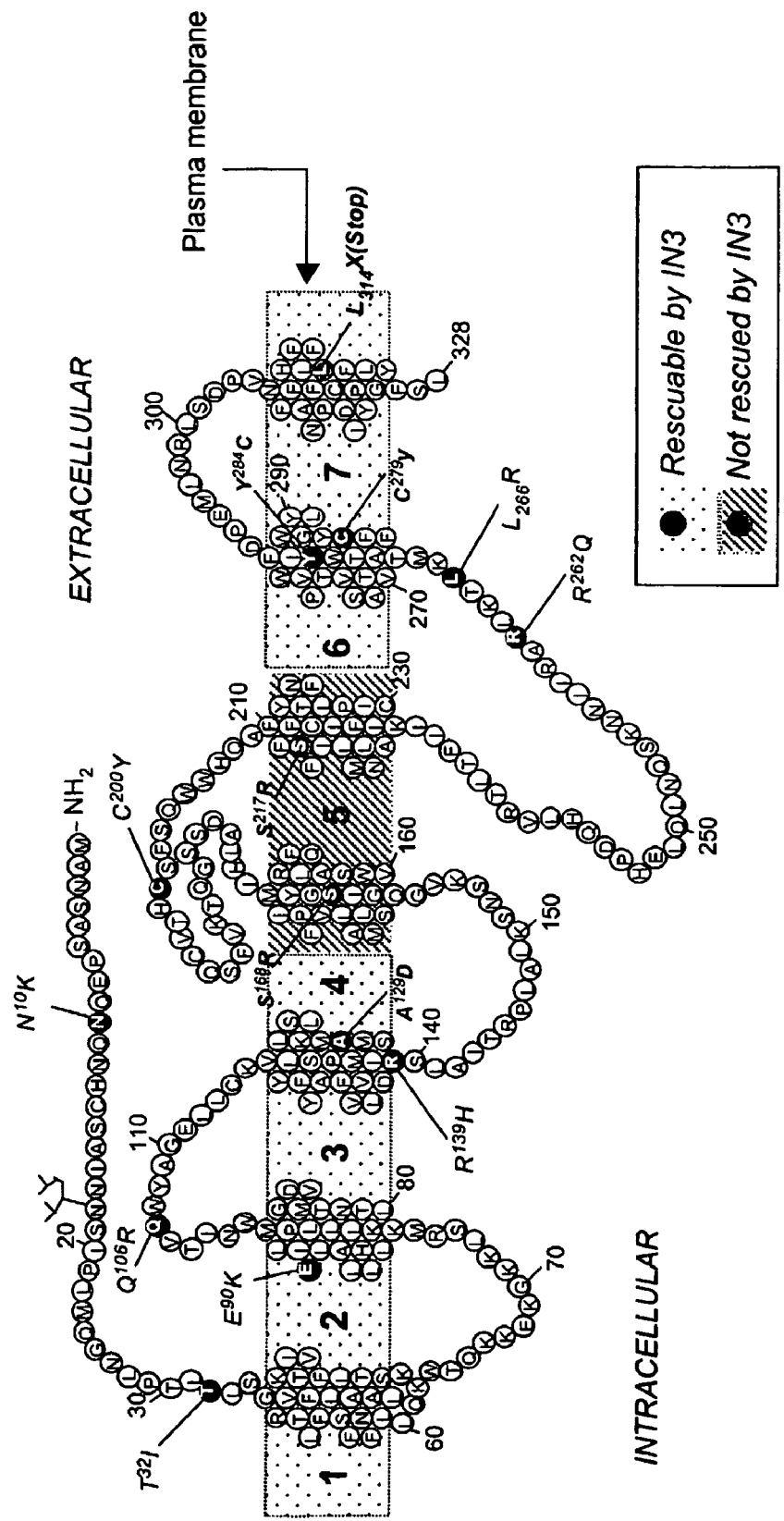
FIG. 1 shows a schematic representation of the human GnRH receptor (SEQ ID NO:1) showing the widespread locus of mutations isolated from patients with hypogonadotropic hypogonadism and the Lys191 found in the human GnRHR, but not in preprimate mammals.

The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. For example, reference to "a mimetic" includes a plurality of such mimetics and reference to "the receptor" includes reference to one or more receptors and equivalents thereof known to those skilled in the art, and so forth.

Unless explained otherwise, all technical and scientific terms used herein have the same meaning as commonly understood to one of ordinary skill in the art to which this disclosure belongs.

Agent: Any polypeptide, compound, small molecule, organic compound, salt, polynucleotide, peptidomimetic, or other molecule of interest.

Binding: A specific interaction between two molecules, such that the two molecules interact. Binding can be specific and selective, so that one molecule is bound preferentially when compared to another molecule. In one embodiment, specific binding is identified by a disassociation constant ($K_d$).

Comprises: A term that means "including." For example, "comprising A or B" means including A or B, or both A and B, unless clearly indicated otherwise.

IN3: Includes [(2S)-2-[5-[2-(2-azabicyclo[2.2.2]oct-2-yl)-1,1-dimethyl-2-oxoethyl]-2-(3,5-dimethylphenyl)-1H-indol-3-yl]-N-(2-pyridin-4-ylethyl)propan-1-amine] and mimetics thereof that can rescue a mutant GnRHR. In one example IN3 does not rescue S$^{168}$R or S$^{217}$R GnRHR mutants, but is capable of rescuing one or more of the following mutants: N$^{10}$K, T$^{32}$I, E$^{90}$K, Q$^{106}$R, A$^{129}$D, R$^{139}$H, C$^{200}$Y, R$^{262}$Q, L$^{266}$R, C$^{279}$Y, or Y$^{284}$C. Ideally, such mimetics are not agonists, since once receptor rescue occurred, the development of the desensitize state would be promoted. In one example, an IN3 mimetic supports scaffolding of the active configuration of GnRHR without occupying the GnRHR active site, and would not need to be removed prior to agonist activation.

Mammal: This term includes both human and non-human mammals. Similarly, the terms "patient," "subject," and "individual" includes both human and veterinary subjects.

Mutant GnRHR: A wild-type GnRHR sequence that includes at least one amino acid substitution or deletion, which results in the development of HH in a subject.

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Rescue: In one example, an agent, such as IN3 (or mimetic thereof), is said to rescue a mutant GnRHR when contact of IN3 with a mutant GnRHR results in increased binding of the mutant receptor to a GnRHR agonist (such as buserelin), as compared to binding in the absence of the agent. For example, binding of a GnRHR agonist to a rescued mutant GnRHR increases at least 25% when compared to binding of a non-rescued mutant GnRHR to GnRHR agonist. In other non-limited examples, binding of a GnRHR agonist to a rescued mutant GnRHR increases at least 50%, such as at least 60%, such as at least 75%, such as at least 80%, such as at least 90%, such as at least 100%, or even such as at least 200%, when compared to binding of a non-rescued mutant GnRHR to GnRHR agonist. Such binding can be performed using the methods disclosed herein (see Example 1).

In another or in an additional example, an agent, such as IN3 (or mimetic thereof), is said to rescue a mutant GnRHR when contact of IN3 with a mutant GnRHR results in an increase in GnRH agonist-stimulated inositol phosphate (IP) production, as compared to IP production in the absence of the agent. For example, IP production by a rescued mutant GnRHR increases at least 25% when compared to IP production by a non-rescued mutant GnRHR. In other non-limited examples, IP production by a rescued mutant GnRHR increases at least 50%, such as at least 60%, such as at least 75%, such as at least 80%, such as at least 90%, such as at least 100%, such as at least 200%, or even such as at least 500% when compared to IP production by a non-rescued mutant GnRHR. Determination of IP production can be performed using the methods disclosed herein (see Example 2).

In another or in an additional example, an agent, such as IN3 (or mimetic thereof), is said to rescue a mutant GnRHR when contact of IN3 with a mutant GnRHR results in increased surface-bound receptor-ligand complex internalized, as compared to an amount of surface-bound receptor-ligand complex internalized in the absence of the agent. For example, surface-bound receptor-ligand complex internalized by a rescued mutant GnRHR increases at least 25% when compared to surface-bound receptor-ligand complex internalized by a non-rescued mutant GnRHR. In other non-limited examples, surface-bound receptor-ligand complex internalized by a rescued mutant GnRHR increases at least 50%, such as at least 60%, such as at least 75%, such as at least 80%, such as at least 90%, such as at least 100%, or even such as at least 200% when compared to an amount of surface-bound receptor-ligand complex internalized by a non-rescued mutant GnRHR. Determination of surface-bound receptor-ligand complex internalized can be performed using the methods disclosed herein (see Example 5).

Subject: Living multicellular vertebrate organisms, a category which includes, both human and veterinary subjects for example, mammals, rodents, and birds.

Therapeutically Effective Amount: An amount sufficient to achieve a desired biological effect. In one example, it is an amount that is effective to increase binding of a GnRHR agonist to a mutant GnRHR by more than a desired amount, increase GnRH agonist-stimulated inositol phosphate (IP) production by a mutant GnRHR by more than a desired amount, and/or increase surface-bound mutant receptor-ligand complex internalized by more than a desired amount. In particular examples, it is a concentration of IN3 or biologically active mimetic thereof that is effective to increase binding of a GnRHR agonist to a mutant GnRHR, increase GnRH agonist-stimulated IP production by a mutant GnRHR, and/or increase surface-bound mutant receptor-ligand complex internalized, such as a cell in a subject to whom it is administered.

In one example, a therapeutically effective amount also includes a quantity of IN3 (including biologically active mimetics thereof) sufficient to achieve a desired effect in a subject being treated. In another or additional example, the therapeutically effective amount also includes a quantity of IN3 (including mimetics thereof) sufficient to achieve a desired effect in a subject being treated. For instance, these can be an amount necessary to improve signs and/or symptoms a disease such as HH, for example by resucing a mutant GnRHR.

An effective amount of IN3 (including biologically active mimetics thereof) can be administered in a single dose, or in several doses, for example daily, during a course of treatment. However, the effective amount will be dependent on the source of IN3, the subject being treated, the severity and type of the condition being treated, and the manner of administration. For example, a therapeutically effective amount of IN3 can vary from about 0.01 mg/kg body weight to about 1 g/kg body weight.

The IN3 molecules and biologically active mimetics thereof disclosed herein have equal application in medical and veterinary settings. Therefore, the general term "subject being treated" is understood to include all animals (e.g. humans, apes, dogs, cats, horses, and cows) that require rescue of one or more mutated GnRHRs.

Therapeutically effective dose: A dose sufficient to rescue a mutant GnRHR (except $S^{168}$ or $S^{217}R$ mutants), resulting in a regression of a pathological condition, or which is capable of relieving signs or symptoms caused by the condition, such as HH.

IN3 Rescues Several Mutant GnRHR Molecules

GnRHR mutants appear to retain intrinsic hormone binding and effector coupling activity and yet due to mutation, are misfolded and appear to not be appropriately positioned at the plasma membrane. Misrouting may include the positioning of a mutant receptor in the plasma membrane in a position that is unavailable to the ligand for binding or to the effector or G-proteins. Correction of such folding defects may restore activity and rescue GnRHR mutants. Disclosed herein in the use of IN3 as a pharmacological agent, which served as a template for the nascent receptor and rescued mutant receptors.

The present disclosure shows the efficacy of IN3, which significantly rescues 11 missense mutations (assessed by both radioligand binding and by IP production). Such rescue occurred despite widely disparate loci along the receptor (FIG. 1). The large proportion of HH GnRHR mutants that could be rescued by the use of a single agent, IN3, demonstrates the significant therapeutic potential of this approach. In addition, many altered receptors (terminally truncated, internal deletions, or lacking the ability to form bridges to form tertiary structure) were also rescued with IN3. Therefore, HH receptor mutants may be frequently misrouted or mispositioned molecules, yet otherwise fully competent to bind ligand and couple to effectors. The data disclosed herein indicates that the misfolding of GnRHR is the causative event, resulting in diminished or lost function in the vast majority of reported naturally occurring GnRHR mutants.

$N^{10}K$, $T^{32}I$, $Q^{106}R$, $R^{262}Q$, and $Y^{284}C$ GnRHR mutants express at the cell surface (FIGS. 2-5), but show sub-optimal ligand binding. Incubation with IN3 restored both ligand binding and IP production. IN3 may lead to the accumulation of more receptors, preventing intracellular degradation of misfolded mutants or WT GnRHRs.

$A^{129}D$, $R^{139}H$, $C^{200}Y$, $L^{266}R$, and $C^{279}Y$ mutant receptors show neither ligand binding nor IP production. These mutants were rescued by IN3 and showed increases in binding and IP production compared to the unrescued state, however, their responses were lower than WT. $S^{168}R$ and $S^{217}R$ mutants were unrescuable with IN3; these mutants showed neither ligand binding nor IP production.

Given the functional characteristics of receptors in the unrescued state and the effect of IN3 on the naturally-occurring GnRHR mutants, a classification of GnRHR mutants is disclosed.

Type I. Defective binding, processing and/or function: $S^{168}R$ and $S^{217}R$.

Type II. Defective intracellular transport by misfolding:

IIa. Misfolding with abnormal trafficking: $E^{90}K$

IIb. Misfolding with increased degradation: $N^{10}K$, $T^{32}I$, $Q^{106}R$, $R^{262}Q$, and $Y^{284}C$.

Type III. Defective binding, processing and/or function with defective intracellular transport by misfolding: $A^{129}D$, $R^{139}H$, $C^{200}Y$, $L^{266}R$, and $C^{279}Y$.

Disclosed herein is a method of rescuing a mutant GnRHR. The method includes contacting a cell expressing the mutant GnRHR with a therapeutic amount of IN3, or a mimetic of IN3 that retains the ability to rescue mutant GnRHR. In one example, the GnRHR mutant includes a $N^{10}K$, $T^{32}I$, $E^{90}K$, $Q^{106}R$, $A^{129}D$, $R^{139}H$, $C^{200}$, $R^{262}Q$, $L^{266}R$, $C^{279}Y$, or $Y^{284}C$ mutation. In another example, the GnRHR mutant does not include a $S^{168}R$ or a $S^{217}R$ mutation.

In a particular example, rescue of mutant GnRHR results in an at least 25% increased binding of the mutant receptor to buserelin, when compared to binding in the absence of IN3. In another or an additional example, rescue of mutant GnRHR results in an at least 25% increased GnRH agonist-stimulated IP production, when compared to IP production in the absence of IN3. In another or an additional example, rescue of mutant GnRHR results in an at least a 25% increase in surface-bound receptor-ligand complex internalized, when compared to surface-bound receptor-ligand complex internalized in the absence of IN3. Contacting the cell with a therapeutic amount of IN3 can include administering IN3 to a subject, such as a human, having HH. In particular examples, IN3 is present in a pharmaceutically acceptable carrier and/or with other therapeutically effective agents.

Example 1

Saturation Binding of Wild-Type and Mutant GnRHR

FIG. 1 shows a representation of the human GnRH receptor indicating several loci of mutation which result in hypogonadotropic hypogonadism (HH). In addition, FIG. 1 shows the Lys[191] found in human GnRHR, but not in preprimate species. It was previously shown that the $E^{90}K$ mutation itself, while resulting in protein misfolding, does not irreversibly destroy the intrinsic ability of the mutant receptor to bind ligand or to couple effector (Maya-Nudez et al., *J. Clinical Endocrinol. Metab.* 87:2144-9, 2002). To demonstrate that mutations in GnRHR result in misrouting of the mutant receptor within the cell, which can be rescued by addition of IN3, the methods below were used. IN3 [(2S)-2-[5-[2-(2-azabicyclo[2.2.2]oct-2-yl)-1,1-dimethyl-2-oxoethyl]-2-(3,5-dimethylphenyl)-1H-indol-3-yl]-N-(2-pyridin-4-ylethyl) propan-1-amine] is an indole previously designed as a peptidomimetic antagonist of GnRH by Merck Research Laboratories in Rahway, N.J. (de Roux et al., *N. Engl. J. Med.* 337:1597-1602, 1997; Layman et al., *Nature Genetics* 18:14-5, 1998; Caron et al., *J. Clin. Endocrinol. Metab.* 84:990-6, 1999).

The following vectors were generated and subsequently transfected into COS-7 cells. Wild-type (WT) hGnRHR cDNA in pcDNA3 was subcloned into pcDNA3.1 at Kpn1 and Xba1 restriction enzyme sites. The E90 to K90 (GAG to AAG) mutation was constructed by overlap extension PCR (Horton et al., *Methods Enzymol.* 217:270-9, 1993). Other GnRHR mutants (see FIG. 1 and Example 4) were prepared by analogous processes (see also Janovick et al., *J. Clin. Endocrinol. Metab.* 87:3255-62, 2002). Rodent sequences (rGnRHR) were expressed in the vector pTracer-CMV; exchange experiments demonstrated that both vectors expressed at equivalent levels in COS-7 cells. The identity of all constructs and the correctness of the PCR-derived sequences were verified by Dye Terminator Cycle Sequencing according to the manufacturer's instructions (Perkin-Elmer, Foster City, Calif.).

For transfection, large-scale plasmid DNAs were prepared using a Qiagen Endotree Maxi-prep kit (Qiagen, Valencia, Calif.). The purity and identity of the amplified plasmid DNAs were further verified by restriction enzyme analysis. Wild-type hGnRHR and mutated receptors were separately transiently expressed in COS-7 cells as previously described (Janovick et al., *J. Clin. Endocrinol. Metab.* 87:3255-62, 2002). Briefly, cells were maintained in growth medium (DMEM) containing 10% fetal calf serum (FCS; Life Technologies, Grand Island, N.Y.) and 20 µg/ml gentamicin (Gemini Bioproducts, Calabasas, Calif.) in a 5% $CO_2$ humidified atmosphere at 37° C. One hundred thousand cells/well were seeded in 24-well plates (Costar, Cambridge, Mass.). Twenty-four hours after plating, the cells were transfected with 0.05 µg DNA per well [for inositol phosphates (IP) or 0.1 µg DNA per well (for saturation binding studies) using 2 µl lipofectamine in 0.25 ml OPTI-MEM containing 1% DMSO (vehicle) or 1 µg/ml IN3 prepared in vehicle. After five hours (see FIG. 3 period 'A'), 0.25 ml of DMEM containing 20% FCS with or without IN3 (as indicated) was added to each well. The cells were incubated for an additional 18 hours (FIG. 3 period 'B') at 37° C., then washed and fresh growth medium with (1 µg/ml) or without IN3 was added to the cells for another 28 hours (FIG. 3 period 'C') at 37° C. The cells were then washed twice with DMEM/0.1% BSA/Gentamicin and were preloaded with $^3$H-inositol (for IP assays, see Example 2) or DMEM (for internalization studies, see Example 5) for 18 hours prior to stimulation with agonist. During this latter 18 hour period, as well as the period of GnRH stimulation, IN3 was not present.

To determine the saturation binding, the cells were washed twice with warm DMEM/BSA prior to incubating with the GnRH agonist [$^{125}$I]-buserelin [D-tert-butyl-Ser$^6$, des-Gly$^{10}$, Pro$^9$, ethylamide-GnRH; specific activity, 700 µCi/µg; 230,000 cpm/0.5 ml, pH 7.4; Hoechst-Roussel Pharmaceuticals (Somerville, N.J.); also see Marian et al., *Mol. Pharmacol.* 19:399-405, 1981] and nonspecific binding was measured in the presence of 1 µM GnRH. Cells were incubated at room temperature for 90 minutes. The medium was removed, plates containing the cells were placed on ice and washed twice with ice-cold PBS. Then, 0.2 M NaOH/0.1% SDS (Costa et al., *J Clin. Endocrinol. Metab.* 86:2680-6, 2001) was added to the wells to solubilize the cells. The sample was transferred to a glass tube and counted in a gamma counter (Packard Instruments; Downers Grove, Ill.). Specific binding was calculated by subtracting non-specific binding (binding measured in the presence of 1 µM GnRH) from total binding (no GnRH). The data shown herein are the means±SEM from triplicate incubations. In all experiments, the standard deviation was typically less than 10% of the corresponding mean, except at basal levels for which the cpm were extremely low. Each experiment was repeated three or more times with similar results; the results of a single experiment are shown.

Figure 2:
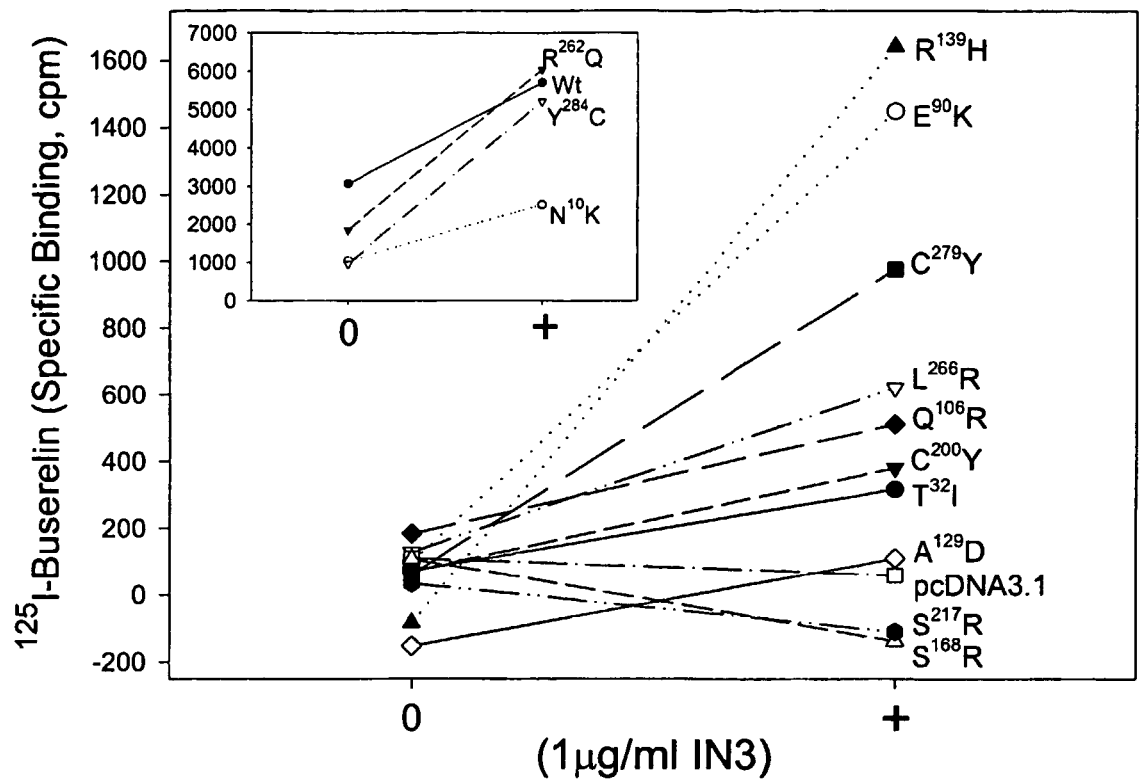
FIG. 2 is a graph showing the specific radioligand binding of [$^{125}$I]-buserelin to COS-7 cells transfected with WT GnRHR, empty vector (pcDNA3.1) or the indicated HH mutants incubated with or without IN3.

As shown in FIG. 2, when 13 hGnRHR mutants identified from different patients with HH were individually expressed in COS-7 cells, no measurable binding was observed. However, addition of IN3 (1 µg/ml) at the time of transfection resulted in significant binding in 11 of 13 of the mutations (FIG. 2), showing that the effect of the mutational error was functionally corrected as assessed by the ability of the mutant receptor to respond to a GnRH agonist. IN3, which is an antagonist, is washed out for 18 hours (even at the longest time present) before exposure to the GnRH agonist. Thus, IN3 not present at the time of the challenge. In contrast, the wild-type hGnRHR showed significant amounts of binding, even in the absence of IN3.

Example 2

Inositol Phosphate Production of Wild-Type and Mutant GnRHR

Figure 3:
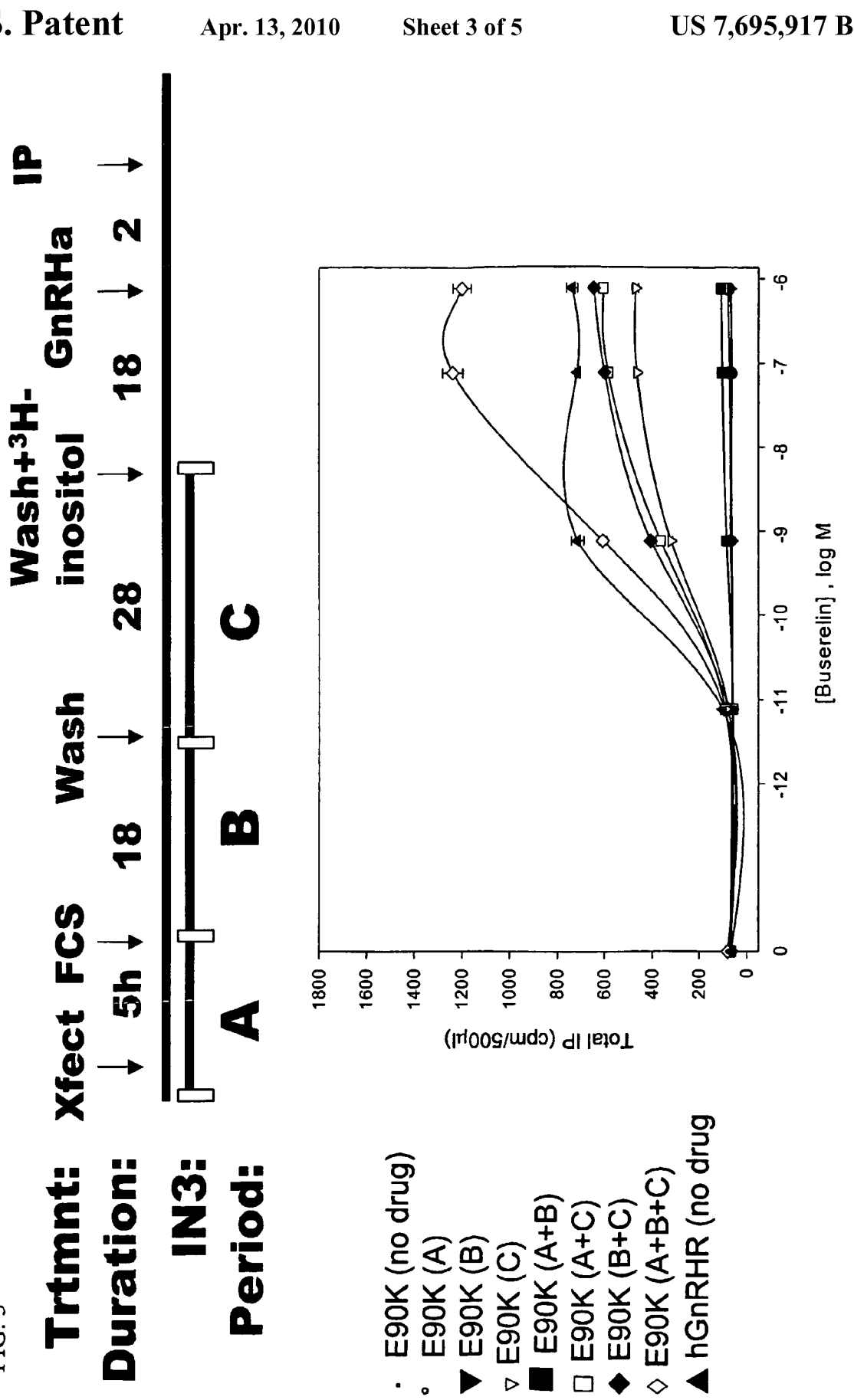

To measure inositol phosphates (IP) production, methods described previously were used (Huckle and Conn, *Methods Enzymol.* 141:149-55, 1987). Briefly, 51 hours after the start of transfection with WT or mutant hGnHRH (as described in Example 1), transiently transfected COS-7 cells were washed twice with DMEM (no IN3) containing 0.1% bovine serum albumin (BSA), and intracellular inositol lipids were incubated in inositol-free DMEM supplemented with 4 µCi/ml [$^3$H]myo-inositol for 18 hours at 37° C. (FIG. 3) (IN3 is no longer present). IN3 was included as indicated in FIG. 3 in single or multiple periods. When the drug was present in multiple periods, fresh IN3 was added at each period. After the preloading period, cells were washed twice with DMEM (inositol free) containing 5 mM LiCl (no IN3) and incubated for 2 hours at 37° C. in the absence or presence of the indicated doses of GnRH agonist buserelin (see Example 1 and FIGS. 3 and 4) dissolved in 0.5 ml DMEM (inositol free)-LiCl. At the end of the incubation period, medium was removed, and 1 ml 0.1 M formic acid was added to each well. Cells were then frozen and thawed to disrupt the cell membranes. IP accumulation was measured by Dowex anion exchange chromatography and liquid scintillation spectroscopy, as previously described (Huckle and Conn, *Methods Enzymol.* 141:149-55, 1987).

To demonstrate the rescue of natural GnRHR mutants by IN3 is specific, experiments were conducted in the presence of a low affinity congener of IN3, IN4 (1-[2-(dimethylamino) ethyl]-2-(3,5-dimethylphenyl)-N,N-diethyl-3-{2-[(4-pyridin-4-ylbutyl)amino]ethyl}-1H-indole-5-carboxamide; $IC_{50}$ for the human receptor is 6450 nM, compared to 0.6 nM for IN3).

Figure 4:
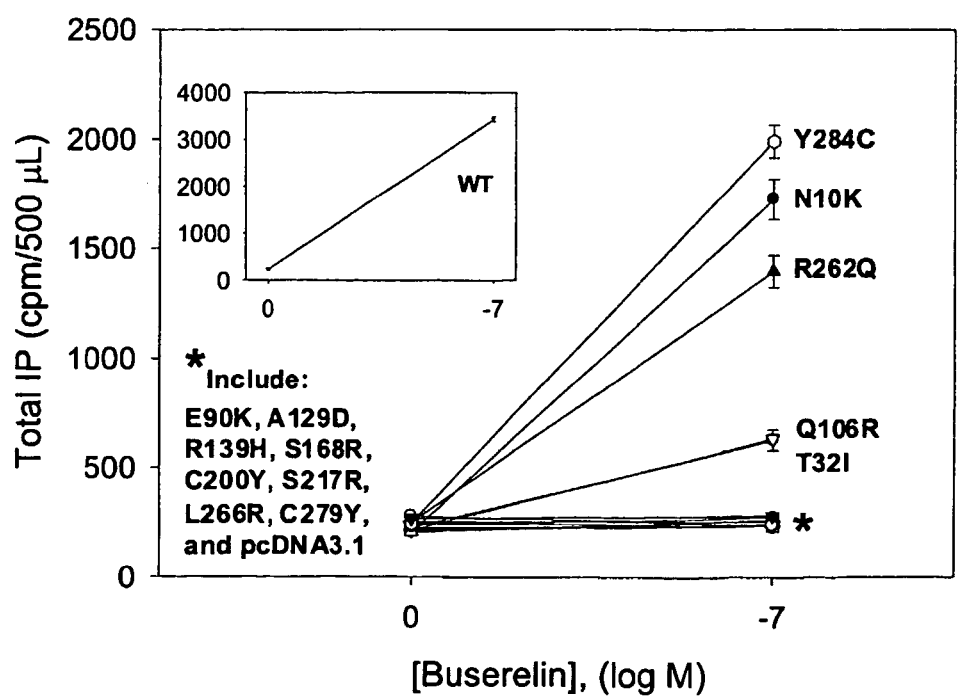
FIGS. 3-5 are graphs showing rescue of mutant hGnRHR with IN3 by measuring stimulation of IP. Standard errors did not exceed 10% of the mean value and the mean of triplicate determinations are shown.

As shown in FIGS. 3 and 4 and Table 1, in contrast to WT, the hGnRHR mutants showed no GnRH agonist-stimulated IP production in the absence of IN3. However, addition of 1 μg/ml IN3 at the time of transfection stimulated IP production in eight mutants ($E^{90}K$, $A^{129}D$, $R^{139}H$, $S^{168}R$, $C^{200}Y$, $S^{217}R$, $L^{266}R$, and $C^{279}Y$), showing that the effect of the mutational error was functionally corrected as determined by the ability to respond to GnRH agonist with IP production. In two mutants, IP production was low compared to WT ($T^{32}I$ and $Q^{106}R$), and in three mutants, was somewhat less than WT ($N^{10}K$, $R^{262}Q$, and $Y^{284}C$) (see FIG. 4).

Figure 5:
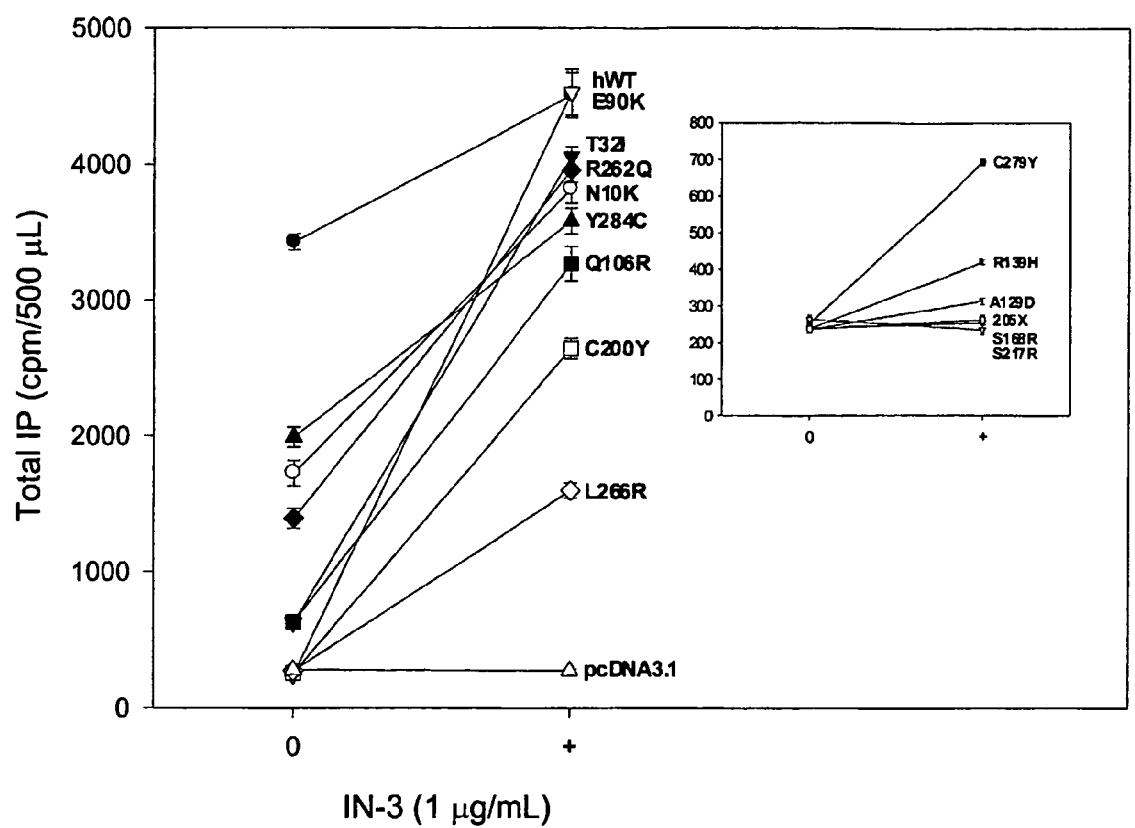

Effector coupling was highest if IN3 was present continuously during the period of transfection and thereafter (see periods A, B and C, FIG. 3). More modest coupling of rescued mutant GnRHR as measured by IP production was observed when IN3 was present only part of the time (FIG. 3). Addition of 1 μg/mL IN3 for 27 hours resulted in a significant increase in IP production in response to buserelin (FIG. 5) for 11 of the 13 GnRHR mutants and for WT. As shown in FIGS. 2 and 5, all mutants with low to modest (i.e. ~37% to 58% compared to WT) IP production and binding prior to treatment were fully rescued and showed similar responses to stimulation as the WT receptor. The other GnRHR mutants, with the exception of $S^{168}R$ and $S^{217}R$, were significantly rescuable.

As shown in Table 1, IN4 was unable to effect rescue at concentrations which were effective for IN3. This specificity indicates that interaction of IN3 with the GnRHR results in stabilization of the GnRHR molecule, and that the action of IN3 is not on receptor (or general) protein synthesis. Neither IN3 nor IN4 induced or inhibited measurable cell proliferation, assessed by cell counting.

Example 3

Specificity of a Rescued $E^{90}K$ hGnRHR Mutant

To compare the rescued mutant $E^{90}K$ receptor with WT GnRHR, ligand specificity and affinity, and receptor features associated with pharmacological disease management, were determined.

COS-7 cells were transfected with vector (0.1 μg cDNA/$10^5$ cells; 2 μl Lipofectamine) as described in the above Examples, and treated with 1 μg/ml IN3 for periods A, B, and C (FIG. 3). The ability of the following agonists (FIG. 6), antagonists (FIG. 7), or irrelevant compounds (FIG. 6) to activate IP production was assessed using the methods described in Example 2: GnRH agonist leuprolide (D-Leu$^6$, Pro$^9$, des-Gly$^{10}$-ethylamide-GnRH; TAP Pharmaceuticals, Deerfield, Ill.); GnRH antagonists (D-Phe$^2$, D-Phe$^6$GnRH, Wyeth-Ayerst Laboratories (Andover, Mass.); 'Nal-Arg' ([Ac-D-Nal$^1$, D-Cpa$^2$, D-Pal$^3$, Arg$^5$, D-Arg$^6$, DAla$^{10}$]-GnRH, Salk Institute); 'Nal-Glu' ([Ac-D-Nal$^1$, D-Cpa$^2$, D-3Pal$^3$, Arg$^5$, D-Glu$^6$, D-Ala$^{10}$]-GnRH, Salk Institute); cetrorelix (Peninsula Laboratories, Inc., San Carlos, Calif.); FE486 [(Ac-D-2Nal$^1$, D-4Cpa$^2$, D-3Pal$^3$, Ser$^4$-4Aph(L-hydroorotyl)$^3$, D4Aph (carbamoyl)$^6$, Leu$^7$, ILys$^8$, Pro$^9$, D-Ala$^{10}$)-GnRH, Ferring Research Institute, Southampton, UK]; azaline B ([Ac-D-Nal$^1$, D-Cpa$^2$, D-Pal$^3$, Aph$^5$ (atz), D-Aph$^6$ (atz), ILys$^8$, DAla$^{10}$]-GnRH); acyline ([Ac-D-2Nal$^1$, D-4Cpa$^2$, D-3Pal$^3$, Ser$^4$Aph(Ac)3$^5$, D-4-Aph(Ac)$^6$, Leu$^7$, Ilys$^8$, Pro$^9$, D-Ala$^{10}$-NH$_2$], Salk Institute); antide, (Serono Laboratories, Aubonne, Switzerland) and irrelevant molecules (GHRP6, octreotide, human galanin, human calcitonin and TSH-releasing hormone (all from Phoenix Pharmaceuticals Inc., Belmont, Calif.), or vapreotide (Debiopharm, Lausanne, Switerzland)).

Figure 6:
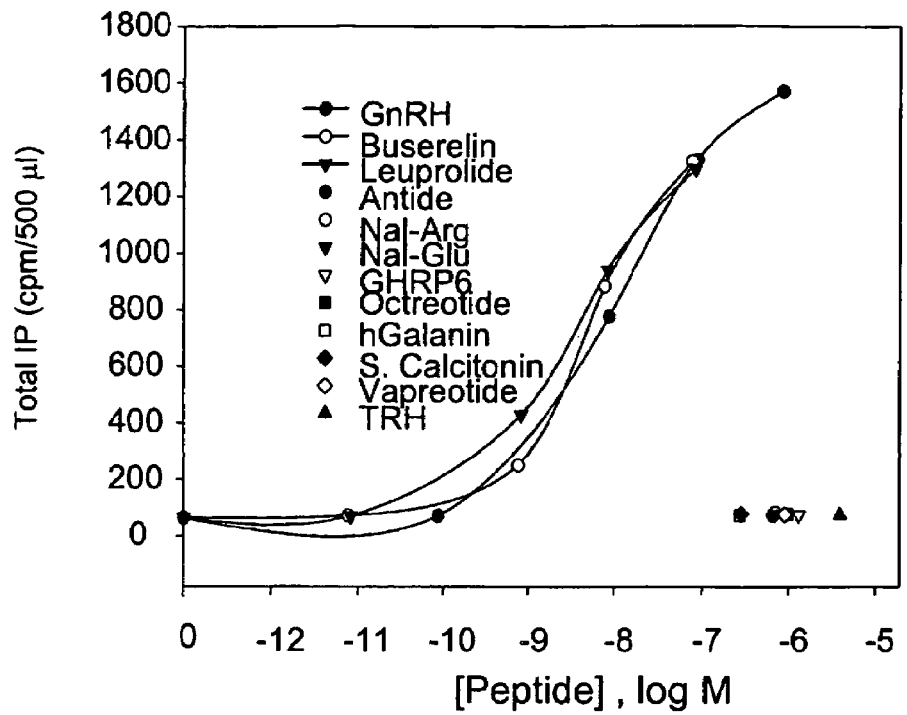
FIGS. 6 and 7 are graphs showing the specificity of the rescued E$^{90}$K hGnRHR. Standard errors did not exceed 10% of the mean value and the mean of triplicate determinations are shown.
Figure 7:
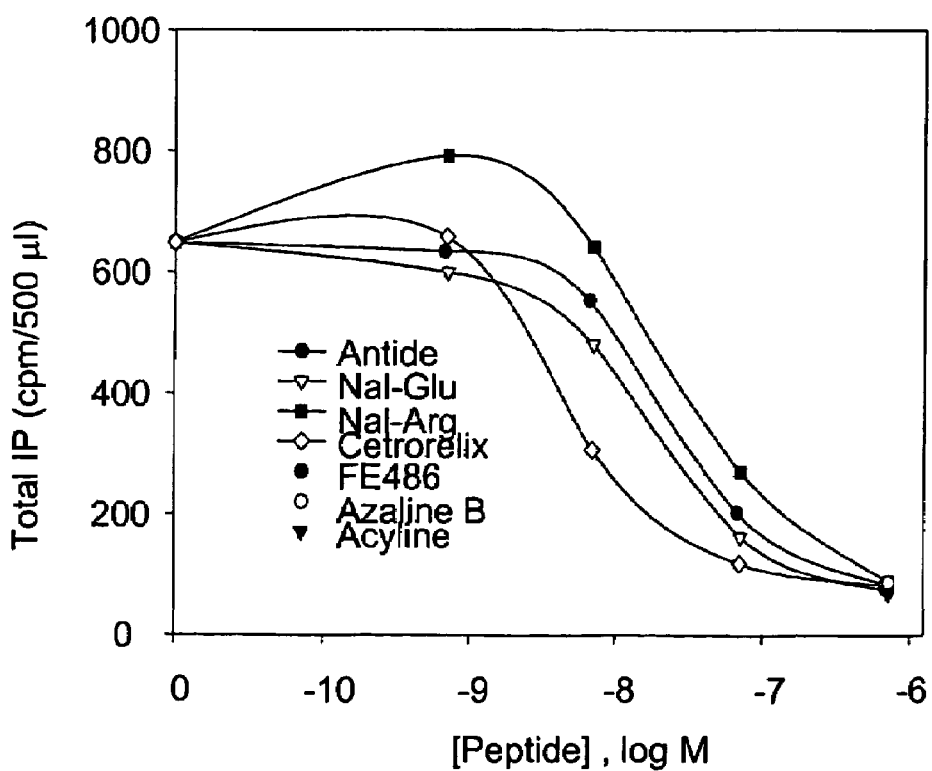

As shown in FIGS. 6 and 7, ligand specificity and the $ED_{50}$ value for the GnRH agonist (4 nM) was indistinguishable from published values for the WT human receptor (Costa et al., *J. Clin. Endocrinol. Metab.* 86:2680-6, 2001; Myburgh et al., *Eur. J Endocrinol.* 139:438-47, 1998) and both GnRH agonists and antagonists were recognized with fidelity and the characteristic varying potencies (Costa et al., *J. Clin. Endocrinol. Metab.* 86:2680-6, 2001; Heding et al., *Endocrinology* 141:299-306, 2000; Vrecl et al., *Mol. Endocrinol.* 12:1818-29, 1998; Millar et al., 1997 Comparative receptor binding affinity and inositol phosphate production potency of D-Leu6 and D-Trp6 GnRH agonists on COS-1 cells transfected with the human GnRH receptor. In: Proceedings of the Thirteenth International Congress of Comparative Endocri-

TABLE 1

IP production by WT and mutant hGnRHRs (in counts per minute).

| | | | IN3 | | | | IN4 | |
| | 0 μg/ml | | 1 μg/ml | | 2.5 μg/ml | | 1 μg/ml | | 2.5 μg/ml |
| Moiety | M* | B | M | B | M | B | M | B | M | B |
|---|---|---|---|---|---|---|---|---|---|---|
| hWT | 106 | 699 | 124 | 1385 | 127 | 1883 | 131 | 645 | 116 | 711 |
| T32L | 115 | 206 | 113 | 1086 | 136 | 1138 | 113 | 192 | 115 | 196 |
| E90K | 116 | 115 | 117 | 1378 | 124 | 1585 | 117 | 114 | 107 | 109 |
| C200Y | 106 | 123 | 123 | 641 | 128 | 777 | 113 | 132 | 105 | 121 |
| L266R | 108 | 105 | 129 | 622 | 125 | 1411 | 112 | 111 | 123 | 121 |
| C279Y | 120 | 112 | 125 | 416 | 132 | 1338 | 118 | 112 | 118 | 121 |

*Cells were prepared and incubated in medium alone (M) or 1 μg/ml buserelin agonist (B).

nology, pp 559-62, Yokohama, Japan; Myburgh et al., *Eur. J. Endocrinol.* 139:438-47, 1998). A selection of irrelevant compounds (not normally bound by the WT receptor) evoked no IP response (FIG. 6).

Example 4

Rescue of Other GnRHR Mutants

As shown in FIGS. 2 (binding) and FIGS. 4, 5 and Table 1 (IP response), at least 11 known genetic mutants of hGnRHR identified from patients with HH and widely distributed on the receptor (N10K, T32I, E90K, Q106R, A129D, R139H, C200Y, R262Q, L266R, C279Y, and Y284C), were fully rescued, as assessed by the ability to respond to GnRH agonist with IP production or by radioligand binding. $C^{200}$ may form a stabilizing bridge to $C^{14}$ (Cook and Eidne, *Endocrinology* 138:2800-6, 1997).

To determine the degree of GnRHR distortion from which rescue could be effected, mutations in the rat GnRHR (rGnRHR) at sites in which a cysteine normally appears were examined, since this amino acid is associated with maintenance of tertiary receptor structure. As shown in Table 2, when varied substitutions were made at the same locus (C278A, C278V, C278T, C278M), there were differences in the ability to effect rescue. The mutants resulting from the more bulky substituents were not formed into the conformation necessary for rescue, and the expression of such variants on the plasma membrane appeared variable in the absence of IN3. Substitution of the bulky Trp at the amino acid 279 (adjacent to $C^{278}$) with Ala ($W^{279}A$) also produced an inactive mutant that was rescued by IN3 (Table 2).

TABLE 2

Attempted rescue of mutant hGnRHRs (in counts per minute).

| | | | IN3 | | | |
|---|---|---|---|---|---|---|
| | 0 | | 1 | | 2.5 | |
| | M* | B | M | B | M | B |
| Cys and adjacent mutants | | | | | | |
| C229A | 157 | 144 | 155 | 152 | 141 | 137 |
| C278A | 132 | 272 | 138 | 2093 | 147 | 2216 |
| C278V | 161 | 144 | 153 | 671 | 143 | 1519 |
| C278T | 144 | 146 | 142 | 826 | 164 | 1102 |
| C278M | 172 | 232 | 154 | 1329 | 132 | 1169 |
| W279A | 152 | 167 | 135 | 1074 | 149 | 1609 |
| Double Mutants | | | | | | |
| C278W/W279C | 148 | 147 | 155 | 152 | 146 | 255 |
| C278V/W279V | 161 | 147 | 153 | 155 | 148 | 475 |
| C278A/W279A | 159 | 148 | 160 | 219 | 148 | 2077 |
| Deletion Mutants | | | | | | |
| Des(237-241) | 104 | 106 | 110 | 319 | 121 | 452 |
| Des(316-327) | 112 | 103 | 105 | 103 | 111 | 107 |
| Des(325-327) | 108 | 122 | 99 | 1031 | 109 | 1605 |

*Cells were prepared and incubated in medium alone (M) or 1 μg/ml buserelin agonist (B).

The double mutants $C^{278}W/W^{279}C$ (exchange of WT sequence) and $C^{278}V/W^{279}V$ were only modestly rescuable (Table 2). In contrast, the double mutant $C^{278}A/W^{279}A$ was restored to full function (Table 2). This difference may reflect the significant steric constraints associated with the larger amino acid residues, Val, Trp and Cys. Ala, in contrast, allows for more freedom of rotation, owing to its smaller size and allowed IN3 to serve as a folding template, resulting in the highest level of IP production. Mutation at $C^{229}$ produced a defect from which rescue could not be effected, indicating that this residue may have other roles in receptor interaction with other molecules.

The shortened carboxyl-terminal truncation mutant [des($^{325-327}$)] showed virtually no response to GnRH when expressed in cultured cells. As shown in Table 2, although deletion of the last three amino acids resulted in loss of IP production in response to the agonist, much of this activity was recovered by IN3. Removing a larger (twelve amino acid) sequence from the carboxyl-terminus [des($^{316-327}$)] produced a mutant that was not rescued, although as many as four amino acids could be removed from the third intracellular loop [des($^{237-241}$)] and rescue still effected by IN3 (Table 2).

Example 5

GnRHR Internalization in the Presence of GnRH Peptide Antagonist

To measure internalization of GnRHR in the presence of other peptide antagonists, the following methods were used. Cells were transfected with mutant or WT hGnRHR as described in Example 1, except that 12 well plates were used and $2 \times 10^5$ cells were plated per well. Each plate served as one time point and contained either WT or mutant receptors transfected into cells using 2 μg plasmid DNA and 5 μl lipofectamine in 0.5 ml OPTI-MEM per well. IN3 (1 μg/ml) or vehicle was present the same amount of time as described for the IP assay (Example 2). Sixty-nine hours after transfection, a previously described radioligand acid wash method (Marian et al., *Mol. Pharmacol.* 19:399-405, 1981; Heding et al., *Endocrinology* 141:299-306, 2000) was used to measure internalization of the mutant or WT human GnRHRs. This method distinguishes internalized and non-internalized receptor. Briefly, cells were washed twice with 0.5 ml DMEM containing 0.1% BSA, then incubated with [$^{125}$I]-buserelin (see Example 1) as noted. At the indicated time, the iodinated ligand was removed and the plate placed on ice. Cells were washed twice with 0.5 ml ice cold PBS, then 0.5 ml acid wash solution (50 MM acetic acid and 150 mM NaCl, pH 2.8) was added to each well and incubated for 12 minutes on ice.

To determine the surface-bound iodinated ligand, the acid wash was collected and counted on a Packard gamma counter (Downers Grove, Ill.). To determine the internalized radioligand-receptor complex, the cells were solubilized in 0.5 ml PBS containing 0.1% Triton-X100, collected and counted. Nonspecific binding for all conditions was determined using the same procedure but in the presence of 10 μM unlabeled GnRH. Nonspecific binding was subtracted from the surface-bound and internalized radioligand, and the amount of internalized radioligand was expressed as the percent internalized of the total bound at each time point.

As shown in Table 3, the percentage of surface-bound receptor-ligand complex internalized by the rescued receptor (40% and 43% at 120 and 160 minutes, respectively), in response to the radioiodinated agonist buserelin was comparable to WT (34% and 40% at 120 and 160 minutes, respectively), excluded the possibility that rescue resulted from stabilization of extant receptor. Likewise, IN3 rescued mutants that were not (previously) measurably expressed on the cell surface (and, therefore not available to be stabilized).

GnRH peptide antagonists were previously designed by chemical analogy to agonists and are therefore expected to bind to the same site, but unlike IN3, cannot permeate cells. As shown in Table 3, these antagonists were unable to rescue HH mutants, deletion mutants, or Cys mutants. The antagonists tested are weak (D-Phe$^2$, D-Phe$^6$-GnRH), intermediate ('Nal-Glu') and high (cetrorelix) affinity binders (Lunenfeld and Insler, GnRH Analogues, The State of the Art, London, The Parthenon Publishing Group, 1993; Bouchard et al., Recent Progress on GnRH and Gonadal Peptides. NY, Elsevier, 1990; Crowley and Conn Modes of Action of GnRH and GnRH Analogues. NY, Springer-Verlag, 1992).

TABLE 3

Failed rescue of hGnRHR by peptide antagonists (in counts per minute).

| Mutant | 0.01 µg/ml* | | 0.1 µg/ml | | 1 µg/ml | | 10 µg/ml | |
|---|---|---|---|---|---|---|---|---|
| | M** | B | M | B | M | B | M | B |
| Ceterelix | | | | | | | | |
| hWT | 71 | 645 | 80 | 677 | 73 | 709 | 76 | 552 |
| E90K | 75 | 73 | 76 | 82 | 70 | 91 | 80 | 103 |
| des325 | 75 | 80 | 83 | 79 | 81 | 82 | 86 | 92 |
| C278W/W279A | 159 | 145 | 130 | 135 | 162 | 150 | 125 | 138 |
| Na-Glu | | | | | | | | |
| hWT | 87 | 629 | 68 | 533 | 82 | 558 | 90 | 660 |
| E90K | 94 | 96 | 80 | 86 | 79 | 100 | 80 | 116 |
| Des325 | 98 | 113 | 91 | 98 | 84 | 94 | 90 | 106 |
| C278W/W279A | 147 | 153 | 172 | 162 | 155 | 155 | 164 | 163 |
| D-Phe2, D-Phe6-GnRH | | | | | | | | |
| hWT | 87 | 869 | 88 | 916 | 76 | 983 | 93 | 1197 |
| E90K | 97 | 86 | 80 | 81 | 84 | 81 | 88 | 101 |
| Des325 | 99 | 106 | 88 | 104 | 87 | 98 | 93 | 124 |
| C278W/W279A | 158 | 164 | 155 | 182 | 147 | 157 | 146 | 144 |
| No Antagonist | | | | | | | | |
| hWT | 91 | 842 | | | | | | |
| E90K | 93 | 99 | | | | | | |
| Des325 | 104 | 109 | | | | | | |
| C278W/W279A | 170 | 156 | | | | | | |

**The indicated GnRH peptide antagonist was included at 0-10 µg/ml as indicated.
*Cells were prepared and incubated in medium alone (M) or 1 µg/ml buserelin agonist (B).

Once rescue by IN3 occurred, the drug was removed for 18 hours prior to stimulation with the GnRH agonist and the receptor remained functional in the membrane, presumably stabilized by hydrophobic membrane interactions. Removal of IN3 is supported by the responsiveness of the rescued receptor to agonists; the IN3 antagonist, if remaining present, is expected to block IP responses in response to GnRH agonist. When IN3 is not removed prior to challenge, the cells are non-responsive.

Example 6

Pharmaceutical Compositions and Modes of Administration

A suitable administration format may be best determined by the subject or by a medical practitioner. In one embodiment, the pharmaceutical compositions that include IN3, or a mimetic thereof, will preferably be formulated in unit dosage form, suitable for individual administration of precise dosages. An effective amount of IN3, or a mimetic thereof, can be administered in a single dose, or in multiple doses, for example daily, during a course of treatment. In one embodiment, IN3, or a mimetic thereof, is administered whenever the effect (e.g., decreased symptoms of HH) is desired. In another embodiment, a time release formulation is utilized.

In one embodiment, a therapeutically effective amount of IN3, or a mimetic thereof, is administered as a single pulse dose, as a bolus dose, or as pulse doses administered over time. Thus, in pulse doses, a bolus administration of IN3, or a mimetic thereof, is provided, followed by a time period wherein no IN3, or a mimetic thereof, is administered to the subject, followed by a second bolus administration. In specific, non-limiting examples, pulse doses of IN3, or a mimetic thereof, are administered during the course of a day, during the course of a week, or during the course of a month.

The therapeutically effective amount of IN3, or a mimetic thereof, can be dependent on the molecule utilized, the subject being treated, the severity and type of the affliction, and the manner of administration, and should be decided according to the judgment of the practitioner and each subject's circumstances. In vitro assays can be employed to identify optimal dosage ranges (see Examples 1-5). Effective doses can be extrapolated from dose-response curves derived from in vitro or animal model test systems. For example, a therapeutically effective amount of IN3, or a mimetic thereof, can vary from about 0.01 µg per kilogram (kg) body weight to about 1 g per kg body weight, such as about 1 µg to about 5 mg per kg body weight, or about 5 µg to about 1 mg per kg body weight. The exact dose is readily determined by one of skill in the art based on the potency of the specific compound (such as IN3, or a mimetic thereof,) utilized, the age, weight, sex and physiological condition of the subject.

The compositions or pharmaceutical compositions can be administered by any route, including intravenous, intraperitoneal, subcutaneous, sublingual, transdermal, intramuscular, oral, topical, transmucosal, or by pulmonary inhalation. Compositions useful in the disclosure may conveniently be provided in the form of formulations suitable for parenteral (including intravenous, intramuscular and subcutaneous), nasal or oral administration. The term "parenteral" refers to modes of administration which include intravenous, intramuscular, intraperitoneal, intrasternal, subcutaneous and intraarticular injection and infusion. IN3, or a mimetic thereof, can be administered subcutaneously. It is well known in the art that subcutaneous injections can be easily self-administered.

In some cases, it will be convenient to provide IN3, or a mimetic thereof, and another therapeutic molecule, such as steroids and gonadotropins, in a single composition or solution for administration together. In other cases, it may be more advantageous to administer the additional agent separately from IN3 (or a mimetic thereof).

A suitable administration format may best be determined by a medical practitioner for each patient individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988.

IN3, or a mimetic thereof, useful in the methods of this disclosure can be provided as parenteral compositions, e.g., for injection or infusion. Preferably, they are suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or "depot" slow release preparation may be used so that therapeutically effective amounts of the preparation are delivered into the bloodstream over many hours or days following transdermal injection or delivery.

IN3, or a mimetic thereof, may be utilized as free bases, as acid addition salts or as metal salts. The salts must, of course, be pharmaceutically acceptable, and these will include metal salts, particularly alkali and alkaline earth metal salts, e.g., potassium or sodium salts. A wide variety of pharmaceutically acceptable acid addition salts are available. Such products are readily prepared by procedures well known to those skilled in the art.

For use by the physician, the compositions can be provided in dosage unit form containing an amount of IN3, or a mimetic thereof, with or without another active ingredient, e.g., a steroid or a gonadotropin. Administration may begin whenever treatment of symptoms associated with HH is desired.

Therapeutically effective amounts of IN3, or a mimetic thereof, are those that rescue a mutant GnRHR by a desired level. As will be recognized by those in the field, an effective amount of therapeutic agent will vary with many factors including the potency of the particular compound, age and weight of the patient, and other factors. Administration may begin whenever rescue of GnRHR and/or treatment of HH is desired.

The optimal formulation and mode of administration of IN3, or a mimetic thereof, to a patient depend on factors known in the art such as the particular disease or disorder, the desired effect, and the type of patient. While the IN3, or a mimetic thereof, will typically be used to treat human subjects they may also be used to treat similar or identical diseases in other vertebrates such as other primates, farm animals such as swine, cattle and poultry, and sport animals and pets such as horses, dogs and cats.

As a pharmaceutical medicament, IN3, or a mimetic thereof, may be administered directly by any suitable technique, including parenterally, intranasally, orally, or by absorption through the skin. The specific route of administration of each agent will depend, e.g., on the medical history of the subject.

For parenteral administration, in one embodiment, IN3, or a mimetic thereof, can be formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. "Pharmaceutically acceptable carrier" refers to a non-toxic solid, semisolid or liquid filler, diluent, encapsulating material or formulation auxiliary of any type.

Generally, the formulations are prepared by contacting IN3, or a mimetic thereof, uniformly and intimately with liquid carriers or finely divided solid carriers or both. Then, if necessary, the product is shaped into the desired formulation. In one example, the carrier is a parenteral carrier, preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

IN3, or a mimetic thereof, can be administered by sustained-release systems. Suitable examples of sustained-release IN3, or a mimetic thereof, include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt). Sustained-release IN3, or a mimetic thereof, compositions may be administered orally, rectally, parenterally, intracistemally, intravaginally, intraperitoneally, topically (as by powders, ointments, gels, drops or transdermal patch), bucally, or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.*15:167-277, 1981; Langer, *Chem. Tech.* 12:98-105, 1982, ethylene vinyl acetate (Langer et al., Id.) or poly-D-(−)-3-hydroxybutyric acid (EP 133,988). Sustained-release IN3, or a mimetic thereof, include liposomally IN3, or a mimetic thereof(see generally, Langer, Science 249:1527-1533, 1990; Treat et al., in *Liposomes in the Therapy of Infectious Disease and Cancer*, Lopez-Berestein and Fidler (eds.), Liss, New York, pp. 317-327 and 353-365, 1989). Liposomes containing IN3, or a mimetic thereof, are prepared by known methods: DE 3,218, 121; Epstein et al., *Proc. Natl. Acad. Sci. U.S.A.* 82:3688-3692, 1985; Hwang et al., *Proc. Natl. Acad. Sci. U.S.A.* 77:4030-4034, 1980; EP 52,322; EP 36,676; EP 88,046; EP 143,949; EP 142,641; Japanese Patent Application No. 83-118008; U.S. Pat. No. 4,485,045, U.S. Pat. No. 4,544,545; and EP 102,324. Ordinarily, the liposomes are of the small (about 200-800 Angstroms) unilamellar type in which the lipid content is greater than about 30 mole percent cholesterol, the selected proportion being adjusted for the optimal performance.

Preparations for administration can be suitably formulated to give controlled release of IN3, or a mimetic thereof. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

In yet an additional embodiment, IN3, or a mimetic thereof, are delivered by way of a pump (see Langer, supra; Sefton, *CRC Crit. Ref. Biomed Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution may also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In another aspect of the disclosure, IN3, or a mimetic thereof, is delivered by way of an implanted pump, described, for example, in U.S. Pat. No. 6,436,091; U.S. Pat. No. 5,939, 380; U.S. Pat. No. 5,993,414. Implantable drug infusion devices are used to provide patients with a constant and long term dosage or infusion of a drug or any other therapeutic agent. Essentially such device may be categorized as either active or passive.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump out the drug from the reservoir, and a catheter port to transport the pumped out drug from the reservoir via the pump to a patient's anatomy. Such devices also typically include a battery to power the pump as well as an electronic module to control the flow rate of the pump. The Medtronic SynchroMed™ pump further includes an antenna to permit the remote programming of the pump. Passive drug infusion devices, in contrast, do not feature a pump, but rather rely upon a pressurized drug reservoir to deliver the drug. Thus, such devices tend to be both smaller as well as cheaper as compared to active devices. An example of such a device includes the Medtronic IsoMed™. This device delivers the drug into the patient through the force provided by a pressurized reservoir applied across a flow control unit.

The implanted pump can be completely implanted under the skin of a patient, thereby negating the need for a percutaneous catheter. These implanted pumps can provide the patient with IN3, or a mimetic thereof, at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump system. Osmotic pumps may be much smaller than other constant rate or programmable pumps, because their infusion rate can be very low. An example of such a pump is described listed in U.S. Pat. No. 5,728,396.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

For administration by inhalation, the compounds for use according to the present disclosure can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch. For inhalation, IN3, or a mimetic thereof, can also be administered as an aerosol or a dispersion in a carrier. In one specific, non-limiting example, IN3, or a mimetic thereof, is administered as an aerosol from a conventional valve, such as, but not limited to, a metered dose valve, through an aerosol adapter also known as an actuator. A suitable fluid carrier can be also included in the formulation, such as, but not limited to, air, a hydrocarbon, such as n-butane, propane, isopentane, amongst others, or a propellant, such as, but not limited to a fluorocarbon. Optionally, a stabilizer is also included, and/or porous particles for deep lung delivery are included (e.g., see U.S. Pat. No. 6,447,743).

The compounds can also be formulated in rectal compositions such as suppositories or retention enemas, e.g., containing conventional suppository bases such as cocoa butter or other glycerides.

In addition to the formulations described above, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions that include IN3, or a mimetic thereof, as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Other medicinal and pharmaceutical agents, for instance other appetite suppressants, or protease inhibitors, also may be included. Actual methods of preparing such dosage forms are known, or will be apparent, to those skilled in the art.

The dosage form of the pharmaceutical composition can be determined by the mode of administration chosen. For instance, in addition to injectable fluids, inhalation, suppository, and oral formulations can be employed. The pharmaceutical compositions can be produced of conventional mixing, granulating, confectioning, dissolving or lyophilizing processes.

Oral formulations may be liquid (e.g., syrups, solutions or suspensions), or solid (e.g., powders, pills, tablets, or capsules). For example, pharmaceutical compositions for oral use can be obtained by combining the active ingredient with one or more solid carriers, optionally granulating a resulting mixture, and, if desired, processing the mixture or granules, if appropriate with the addition of additional excipients, to form tablets or dragee cores.

Suitable carriers include fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose and/or polyvinylpyffolidone, and/or, if desired, disintegrators, such as the above-mentioned starches, also carboxymethyl starch, cross-linked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

For parenteral administration compositions include suitable aqueous solutions of an active ingredient in water-soluble form, for example in the form of a water-soluble salt, or aqueous injection suspensions that contain viscosity-altering substances, for example sodium carboxymethylcellulose, sorbitol and/or dextran, and, if desired, stabilizers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

Compounds with poor solubility in aqueous systems require formulation by using solubilizing agents such as ionic surfactants, cholates, polyethylene glycol (PEG), ethanol, or other agents which may have undesirable effects when used for inhalation. In addition, a treatment requiring successful delivery into alveoli of the lower pulmonary region may preclude from the formulation the use of certain irritants such as chlorofluorocarbons and should involve a minimum number of required doses. Alternatively, to avoid such limitations, liposomes or hydrophobic particles can be used. In one embodiment, an inhalation formulation for a sustained release includes using aerosol droplet particles approximately 1-2.1 µm in size, or of less than 1 µm in size. Small particle aerosol liposomes and liposome-drug combinations for medical use have been previously described (e.g., see EP 87309854.5).

In one embodiment, a therapeutically effective amount of IN3 or a mimetic thereof is administered with a therapeutically effective amount of another agent, such as, but not limited to, a steroid or gonadotropin. IN3 or a mimetic thereof can be administered simultaneously with the additional agent, or they may be administered sequentially. Thus, in one embodiment, IN3 or a mimetic thereof, is formulated and administered with a steroid and/or gonadotropin as a single dose.

Additionally, a method of treating HH is disclosed herein. The method includes administering to a subject having HH a therapeutically effective amount of IN3 or a mimetic thereof. IN3 or a mimetic thereof can be administered in a single or divided dose. Suitable single or divided doses include, but are not limited to, 1 µg to about 5 mg or about 0.01 µg/kg to about 500 µg/kg per dose.

A method of rescuing a mutant GnRHR is also disclosed herein. The method includes contacting a cell expressing a mutant GnRHR (except a $S^{217}R$ or $S^{168}R$ mutation) a therapeutically effective amount of IN3 or a mimetic thereof. IN3 or a mimetic thereof can be administered in a single or divided dose. Suitable single or divided doses include, but are not limited to, 1 µg to about 5 mg or about 0.01 µg/kg to about 500 µg/kg per dose.

In another embodiment, a method is disclosed herein for alleviating a condition or disorder which can be alleviated by rescuing mutant GnRHR (except a S217R or S168R mutation). The method includes administering to a subject a therapeutically effective amount of IN3 or a mimetic thereof. Suitable disorders include any of the disorders mentioned above. IN3 or a mimetic thereof can be administered in a single or divided dose. Suitable single or divided doses include, but are not limited to, 1 µg to about 5 mg or about 0.01 µg/kg to about 500 µg/kg per dose.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

The disclosure provides compositions which include IN3 or mimetics thereof, for example a composition that includes at least 50%, for example at least 90%, of IN3 or a mimetic in the composition. Such compositions are useful as therapeutic agents when constituted as pharmaceutical compositions with the appropriate carriers or diluents.

Example 7

Method for Generating IN3 Mimetics

Also disclosed are biologically active, non-peptide organic molecules that mimic the action of IN3 that can rescue a GnRHR mutant, such as N10K, T32I, E90K, Q106R, A129D, R139H, C200Y, R262Q, L266R, C279Y, or Y284C but not S168R or S217R. The ability of a mimetic of IN3 to rescue a GnRHR mutant can be determined using the methods disclosed herein.

A person of ordinary skill in the art will appreciate that certain structural changes may be made to compounds of the present disclosure, as long as such structural changes do not alter the biological activity of IN3, that is, the ability of IN3 to rescue GnRHR mutants. For example, IN3 includes a number of alkyl substituents, specifically methyl groups, such as the gem dimethyl groups and the methyl group at the chiral center adjacent to the indole. These alkyl substituents may vary in length and position on the molecule, and typically are selected from the group consisting of lower (i.e., ten carbon atoms or fewer) aliphatic groups, more particularly lower alkyl groups, including straight and branched chains, as well as all biologically active stereoisomers. Also, the methyl groups of the 3,5-dimethylbenzene ring can be varied to be other lower aliphatic groups, most likely lower alkyl groups, and the relative positioning of such lower aliphatic groups can be other than 3,5. Additionally, the number of lower aliphatic groups can vary from 1-5.

Moreover, IN3 includes an amide functionality, and such amide can vary from the [2.2.2] bicycloaminooctane moiety of IN3. For example, other cyclic compounds, as well as acyclic amides, may be included. Also, with reference to such amides, the carbonyl oxygen can be replaced with other heteroatoms, most notably sulfur. Also the nitrogen atom of the heterocyclic amines also can vary, and potentially can be replaced with an atom selected from the group consisting of oxygen and sulfur. Furthermore, regioisomers of the oxygen, nitrogen and sulfur heterocycles can replace the heterocyclic amine moieties. Thus, the indole moiety may be replaced by fused bicyclic aromatic moieties, such as benzimidazole, benzofuran, and benzothiophene derivatives. Particular aromatic heterocycles are selected from the group consisting of furan, pyrrole, thiophene, oxazole, imidazole, thiazole, quinoline, isoquinoline, pyrimidine, purine, benzofuran, benzothiophene, and derivatives thereof The hydrogen atom bonded to the nitrogen atom of the aliphatic amine also can be replaced with lower aliphatic substituents, with such substituents typically being selected from the group consisting of lower alkyl groups, with methyl groups being a likely such substituent. The substitution pattern of the pyridine derivative can be varied, for example a 2-pyridine or a 3-pyridine derivative can be used in place of the 4-pyridine moiety of IN3. Additionally, the pyridine moiety can be replaced with another aromatic group, such as a five membered, six membered, or fused aromatic heterocycle. Finally, the number of methylene units spacing particular functional groups and moieties of IN3 can be varied. For example, IN3 includes 2 methylene units that space the amine portion of IN3 from the pyridine ring. The number of methylene units may vary from about 1-10, more typically from about 2-5.

In view of the many possible embodiments to which the principles of this disclosure may be applied, it should be recognized that the illustrated embodiments are only particular examples of the disclosure and should not be taken as a limitation on the scope of the disclosure. Rather, the scope of the disclosure is in accord with the following claims. I therefore claim all that comes within the scope and spirit of these claims.

I claim:

1. An in vitro method of rescuing a mutant gonadotropin-releasing hormone receptor (GnRHR), comprising contacting a cell expressing the mutant GnRHR with [(2S)-2-[5-[2-(2-azabicyclo[2.2.2]oct-2-yl)-1,1-dimethyl-2-oxoethyl]-2-(3,5-dimethylphenyl)-1H-indol-3-yl]-N-(2-pyridin-4-ylethyl)propan-1-amine] (IN3), and rescue of the mutant GnRHR results in an at least 25% increased binding of the mutant receptor to buserelin, an at least 25% increased GnRH agonists-stimulated inositol phosphate (IP) production, or an at least 25% increase in surface-bound receptor-ligand complex internalized, when compared to an absence of IN3.

2. The method of claim 1, wherein the GnRHR mutant includes a $N^{10}K$, $T^{32}I$, $E^{90}K$, $Q^{106}R$, $A^{129}D$, $R^{139}H$, $C^{200}Y$, $R^{262}Q$, $L^{266}R$, $C^{279}Y$, or $Y^{284}C$ mutation.

3. The method of claim 1, wherein the GnRHR mutant includes a $N^{10}K$, $T^{32}I$, $Q^{106}R$, $R^{262}Q$, or $Y^{284}C$ mutation.

4. The method of claim 1, wherein the GnRHR mutant includes an $E^{90}K$ mutation.

5. The method of claim 1, wherein the GnRHR mutant does not include a $S^{168}R$ or a $S^{217}R$ mutation.

6. The method of claim 1, wherein the IN3 is present in a pharmaceutically acceptable carrier.

* * * * *